(12) United States Patent
Garelick et al.

(10) Patent No.: US 7,276,039 B2
(45) Date of Patent: Oct. 2, 2007

(54) GAUNTLET BRACE

(75) Inventors: David H. Garelick, Chicago, IL (US); Edward L. Cotton, South Holland, IL (US); James J. Weber, Santa Barbara, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 433 days.

(21) Appl. No.: 10/856,304

(22) Filed: Jun. 1, 2004

(65) Prior Publication Data

US 2005/0267391 A1    Dec. 1, 2005

(51) Int. Cl.
*A61F 5/00* (2006.01)
*A61F 13/00* (2006.01)
(52) U.S. Cl. .......................... 602/21; 602/64
(58) Field of Classification Search ............ 602/20–22; 128/878, 879; D24/190; 2/16, 159, 161.7
See application file for complete search history.

(56) References Cited

U.S. PATENT DOCUMENTS 5,649,900 A * 7/1997 Kline ........................... 602/21
7,033,331 B1 * 4/2006 Hely ............................ 602/21

* cited by examiner

*Primary Examiner*—Kim M. Lewis
(74) *Attorney, Agent, or Firm*—William W. Haefliger

(57) ABSTRACT

A finger and hand brace, the combination comprising a longitudinally elongated brace body, adapted to be applied lengthwise to the wrist and finger region of the hand; multiple flexible flaps carried by the body to be spaced lengthwise thereof and to extend from the body; separate flaps configured to be wrapped about at least two of the following: hand, wrist, a finger or fingers; and retention means on the brace to retain the flaps in wrapped condition. Elongated, adjustably bendable inserts may be employed to extend in spaced relation in the body, and a thumb hole may be provided in the body, between the inserts.

10 Claims, 12 Drawing Sheets

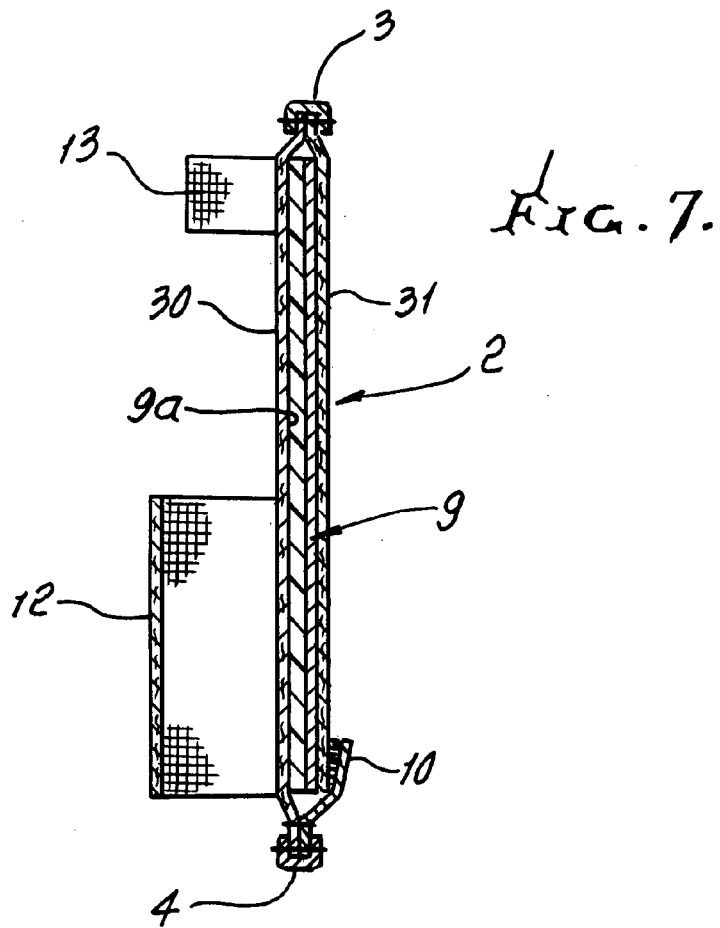
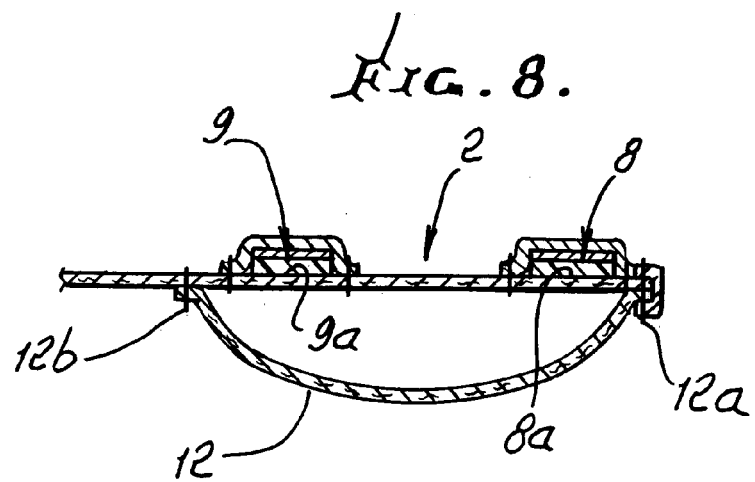

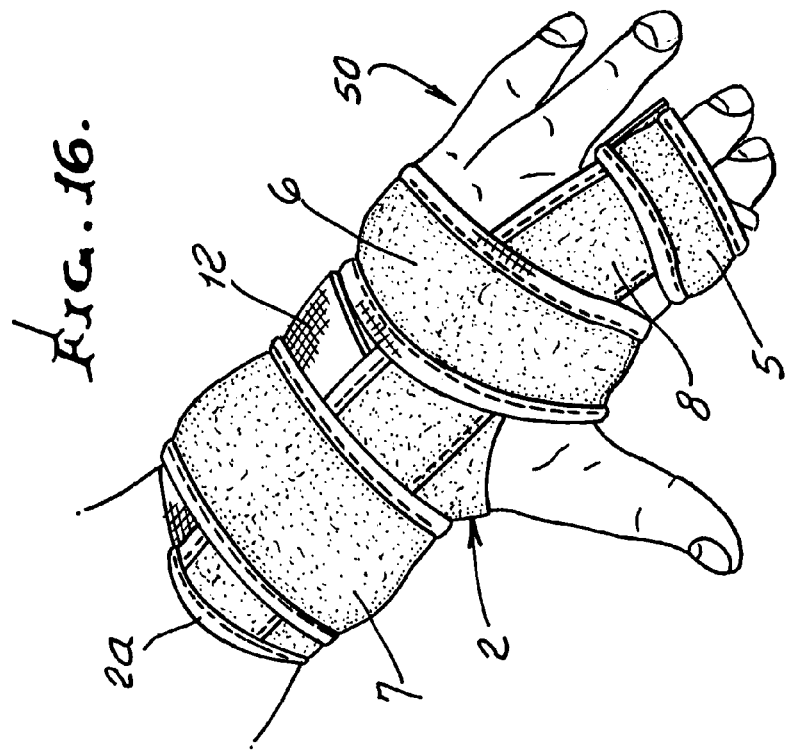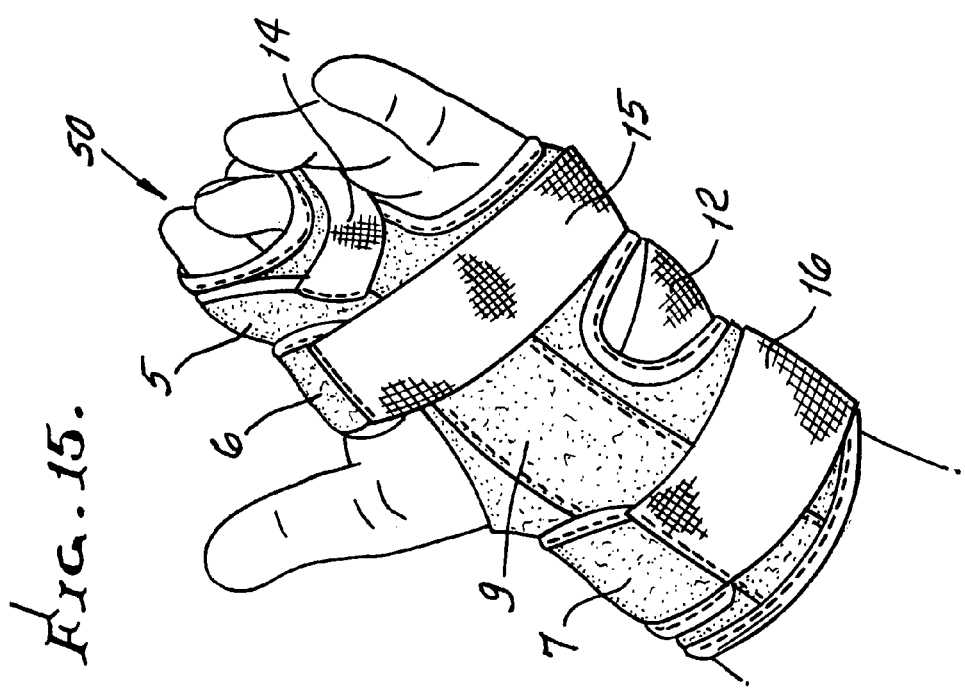

GAUNTLET BRACE

BACKGROUND OF THE INVENTION

The present invention relates generally to a hand, wrist and finger brace, one example being a boxer's fracture brace. More particularly, the present invention relates to an improved brace for temporarily immobilizing the hand in such a way as to allow a fracture of the neck of the fourth, ring finger, or fifth metacarpal, which is the bone in the small finger of the human hand, to heal in a desired manner, with a minimum of disruption in the patient's normal activity.

There are over 1,500,000 metacarpal and phalangeal fractures each year. A large percentage of these involve a fracture of the fourth or fifth metacarpal shaft and neck. This injury is commonly known as a "boxer's fracture", as it is often the result of someone striking or punching an object harder than the hand, such as a wall or another person's head as during boxing. The traditional treatment for such an injury is three to six weeks of cast immobilization. Due to how these types of injuries occur, they are often experienced in younger, more active individuals. In such patient's, there is a high desire and need to return to work and/or physical and athletic activities as quickly as possible. Therefore, there exists a need for treatment of these types of injuries in such a way as to allow an accelerated return to normal activities by the patient in an easy and hand flexible manner.

SUMMARY OF THE INVENTION

The present invention relates to a new, useful and unique hand immobilizing brace that is useful for a large group of patients based upon it's ease of application to the hand, and its moldability to the hand, its flexibility, reversibility and improved healing promotion capabilities. These features will meet a need not currently being met and for the foregoing reasons, this invention is intended to fill this void.

The invention is also directed to a brace enabling a patient to quickly return to normal work and/or physical activities. The versatile, moldable brace is typically configured to immobilize the fourth and fifth metacarpal fractures as well as phalangeal fractures, while at the same time being easily removable from the patient.

It is a further object of this invention that the brace be readily conformable or moldable to easily fit a large number of patients' hands through the use of semi-rigid inserts received in elongated pockets in an elongated brace body. The inserts are positioned to facilitate reversibility of the brace, for use on a fracture of either hand.

These and other objects and advantages of the invention, as well as the details of an illustrative embodiment, will be more fully understood from the following specification and drawings, in which:

DRAWING DESCRIPTION

FIG. 7 is a section taken on lines 7-7 of FIG. 1;

FIG. 8 is a section taken on lines 8-8 of FIG. 2;

FIGS. 9-18 are views showing the brace of the invention applied to left and right hands that have undergone fractures.

DETAILED DESCRIPTION

Figure 1:
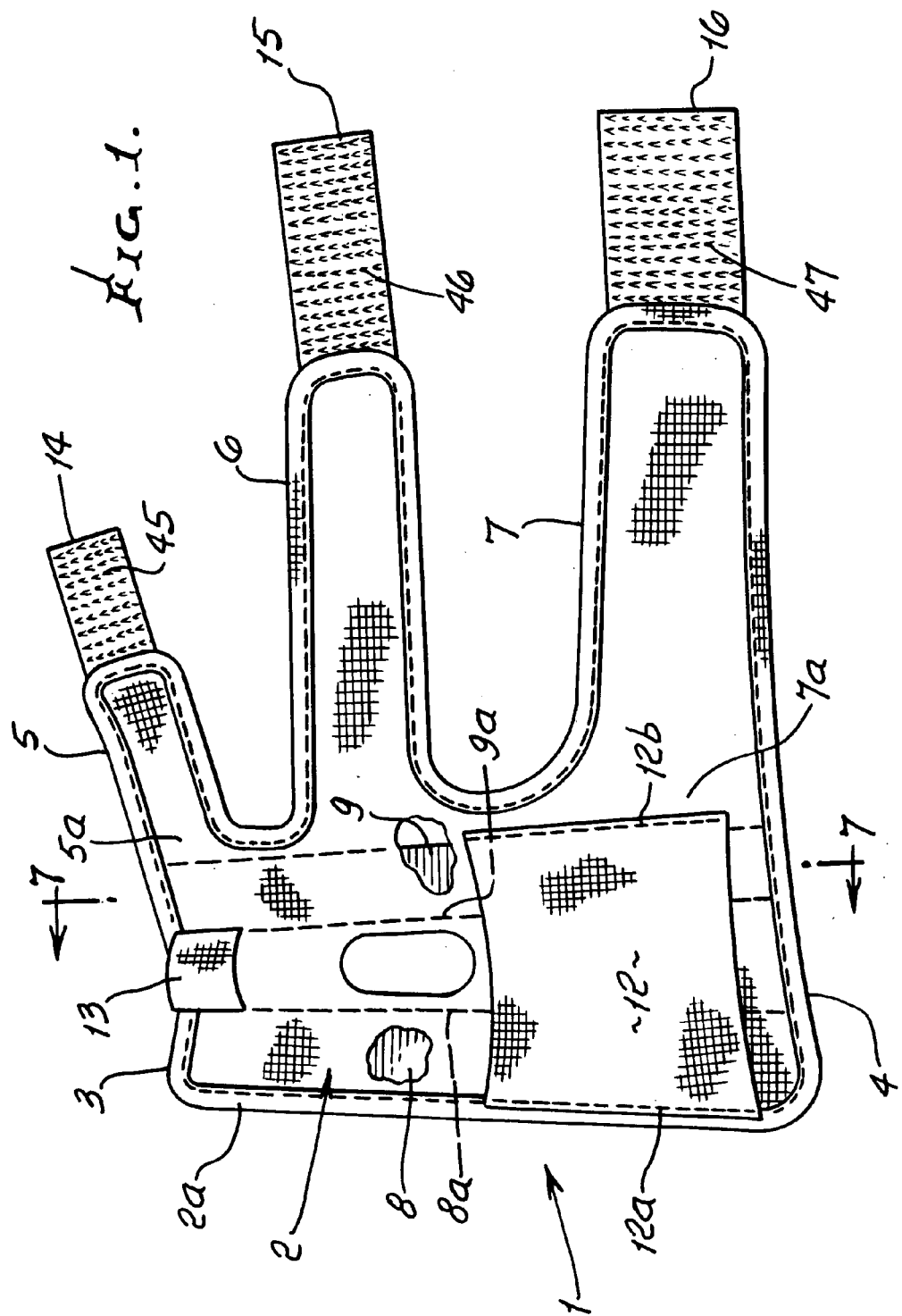
FIG. 1 shows one side of a preferred embodiment of the brace.
Figure 2:
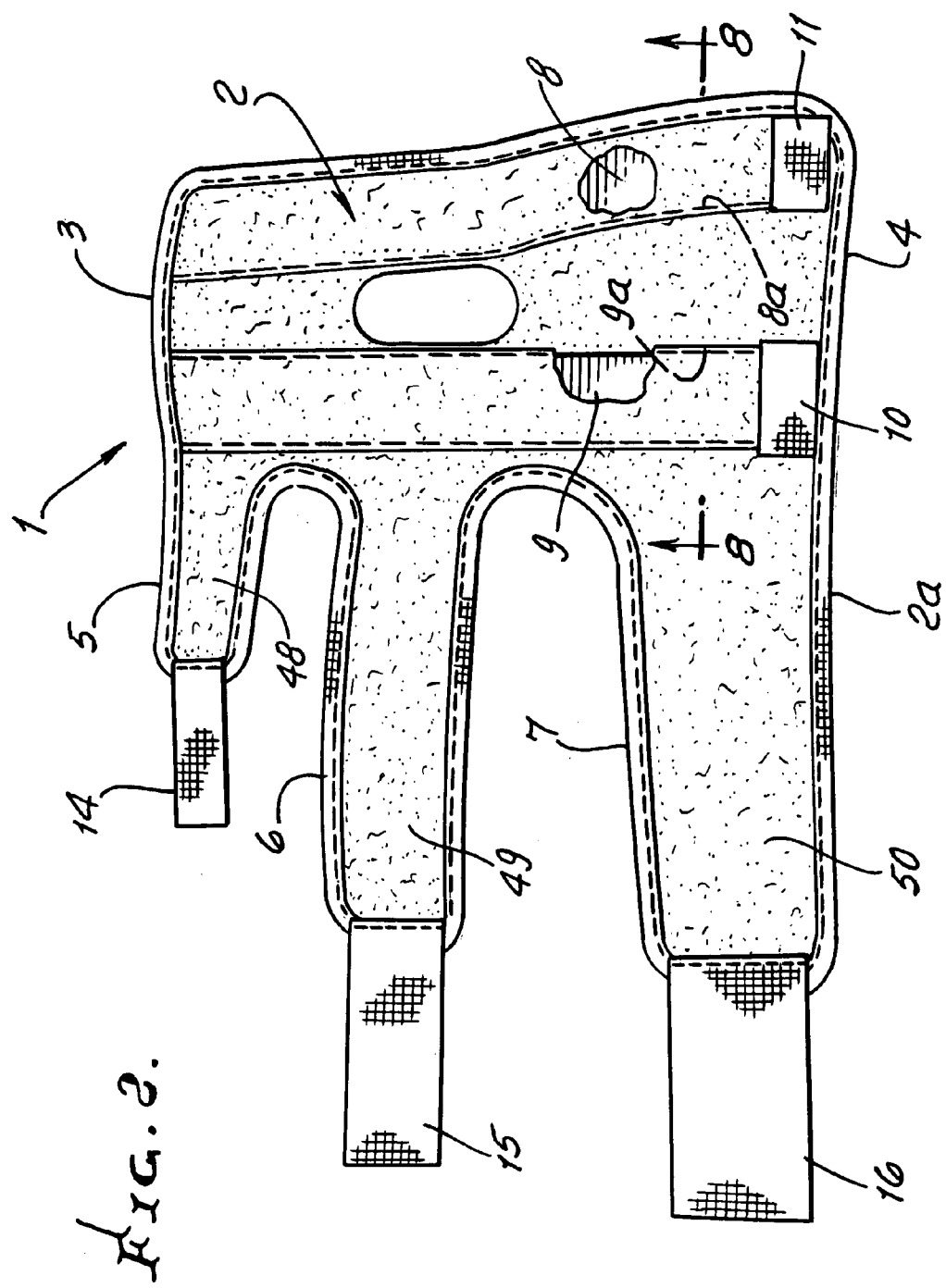
FIG. 2 shows the opposite side of the FIG. 1 brace.

FIGS. 1 and 2 depict two views of one preferred embodiment of the brace 1 of the present invention. FIG. 1 shows the interior view of the brace which is the side of the brace which is placed against the patient's hand and wrist. FIG. 2 shows the exterior view of the FIG. 1 brace which is the opposite side of the brace as shown in FIG. 1.

Brace 1 comprises a longitudinally elongated body or member 2, having a distal end 3 and a proximal end 4. Three or more straps, 5-7, are provided, and positioned along the elongated member 2 to secure a patient's fingers and hand, respectively, to member 2. In this embodiment, the brace is made of a flexible webbing material commonly known in the medical industry, and may have seam binding material 2a extending at the periphery of 2, in bounding relation.

Rigidity for the brace 1 as needed for hand immobilizing is provided by two slat-like elongated inserts 8 and 9 that are inserted in longitudinally elongated and cushioned pockets 8a and 9a on or in the webbing that extend between outer edges of the elongated body member 2, and from the distal end 3 to the proximal end 4. In this embodiment the inserts may be approximately one inch wide and may consist of moldable or malleable (adjustably bendable), semi-rigid metal such as aluminum. One or both inserts can be removed as via slots in the webbing secured by flaps 10 and 11 located at the ends of the pockets at the proximal ends 4 of the elongated members. The flaps 10 and 11 are typically held in closed position by a VELCRO system, or similar hook and pile system. In closed position, the flaps maintain the inserts securely in the pockets in brace 1. Retention of the semi-rigid inserts as described also further enhances the ability of the brace to be reversible, so it can be applied to either the left or right hand of a patient, with no need for two separate braces. For this purpose, the opposite side walls of the pockets are cushioned, as seen at 30 and 31 in FIG. 7.

The brace also carries a sleeve 12 connected at 12a and 12b to the elongated body member 2 near the proximal end 4, such connections extending toward the distal end 3, whereby the sleeve captivates and positions the patients inserted wrist and/or lower hand to provide further stability of the proximal end of the brace relative to the hand and wrist. A smaller sleeve 13 may be provided at or near the distal end 3 of the elongated body member, at or near the center of the elongated body member, and into which the patient's pinky finger is placed or inserted to provide further stability of the fifth metacarpal and the distal end of the brace.

The straps 5, 6, and 7 shown as laterally elongated in FIG. 1, can be any fixable and flexible material, and retained to the member at 5a, 6a and 7a as shown in FIGS. 1 and 2. Each strap 5, 6 and 7 has a locking mechanism at its terminal to vary the length of the strap to fit the hand and wrist of a particular patient. As shown, the locking mechanism comprises hook or pile material 45-47 on tabs 14-16, to press connect to pile or hook material 48 to 50 on the back sides of the straps. Material at 48-50 is extensive in area to allow substantial variability in tab connection locations, accommodating to different hand sizes. It will be understood by those skilled in the art that the straps 5, 6, and 7 and the locking mechanisms 14, 15 and 16 are just one of a group of equivalent devices, for example, VELCRO straps, elastic straps, etc., and all such equivalents are deemed within the scope of the present invention.

Figure 3:
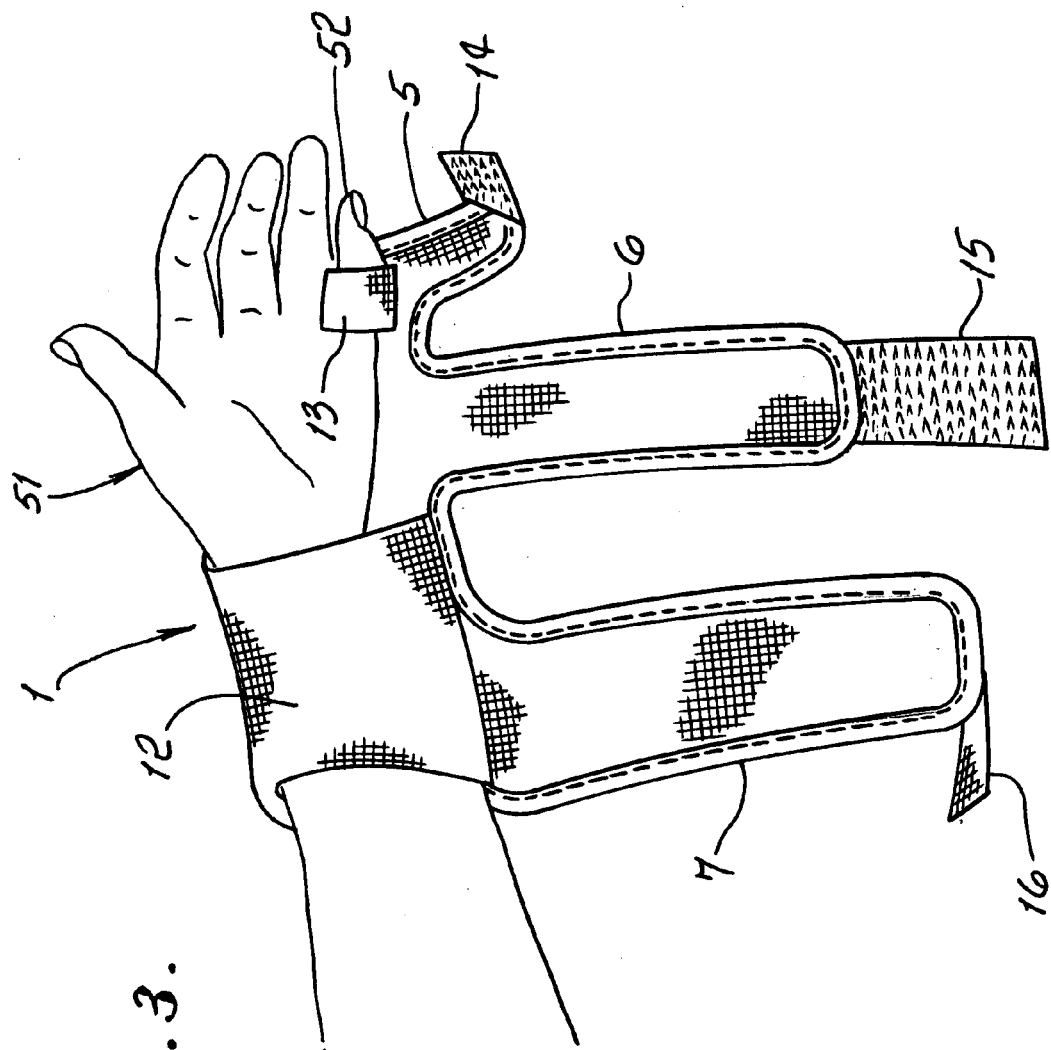
FIG. 3 is a view like FIG. 1, but also showing the brace being applied to a patient's hand.

As shown in FIG. 3, brace 1 is placed on a patient by first inserting the patient's hand 51 through or under sleeve 12 and then further inserting the patient's pinky finger 52 into sleeve 13. In this position the semi-rigid stiffeners of the brace are located on either side of the pinky finger and lower hand. Further in this illustration, none of the straps 5, 6 and 7 have yet been secured.

Figure 4:
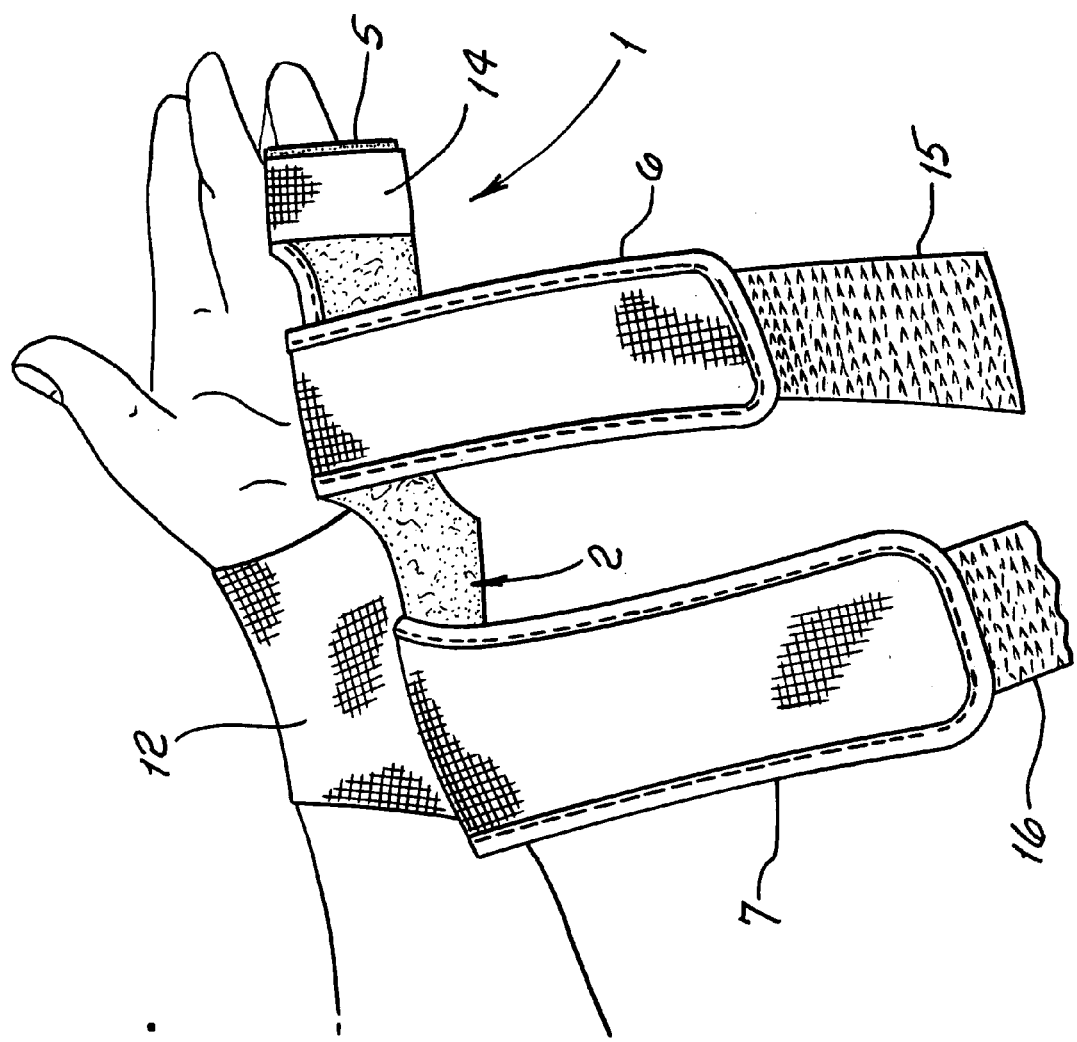
FIG. 4 is a view like FIG. 3, but showing one strap in finger securing position.
Figure 5:
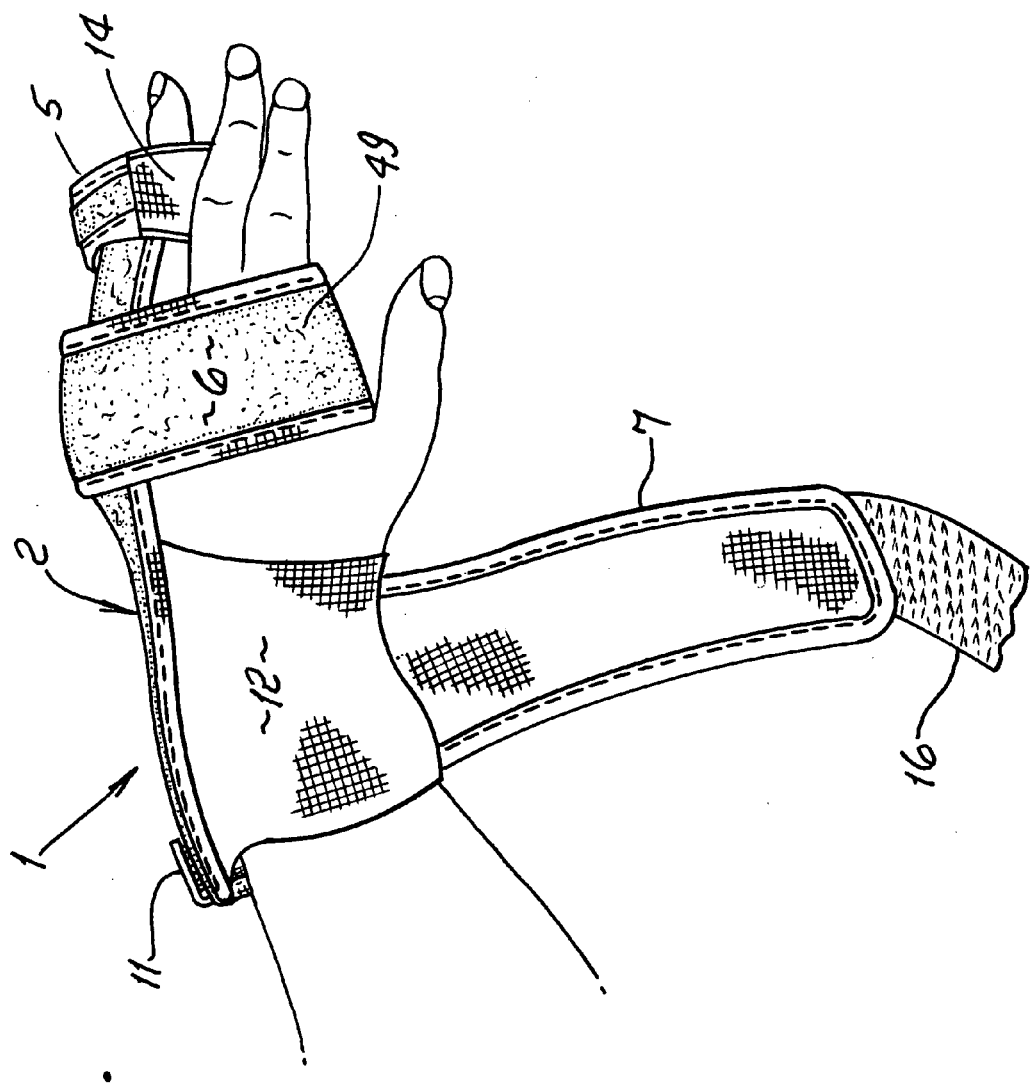
FIG. 5 is a view of the opposite side of the user's hand with two straps wrapped in position, and the third strap partially wrapped.
Figure 6:
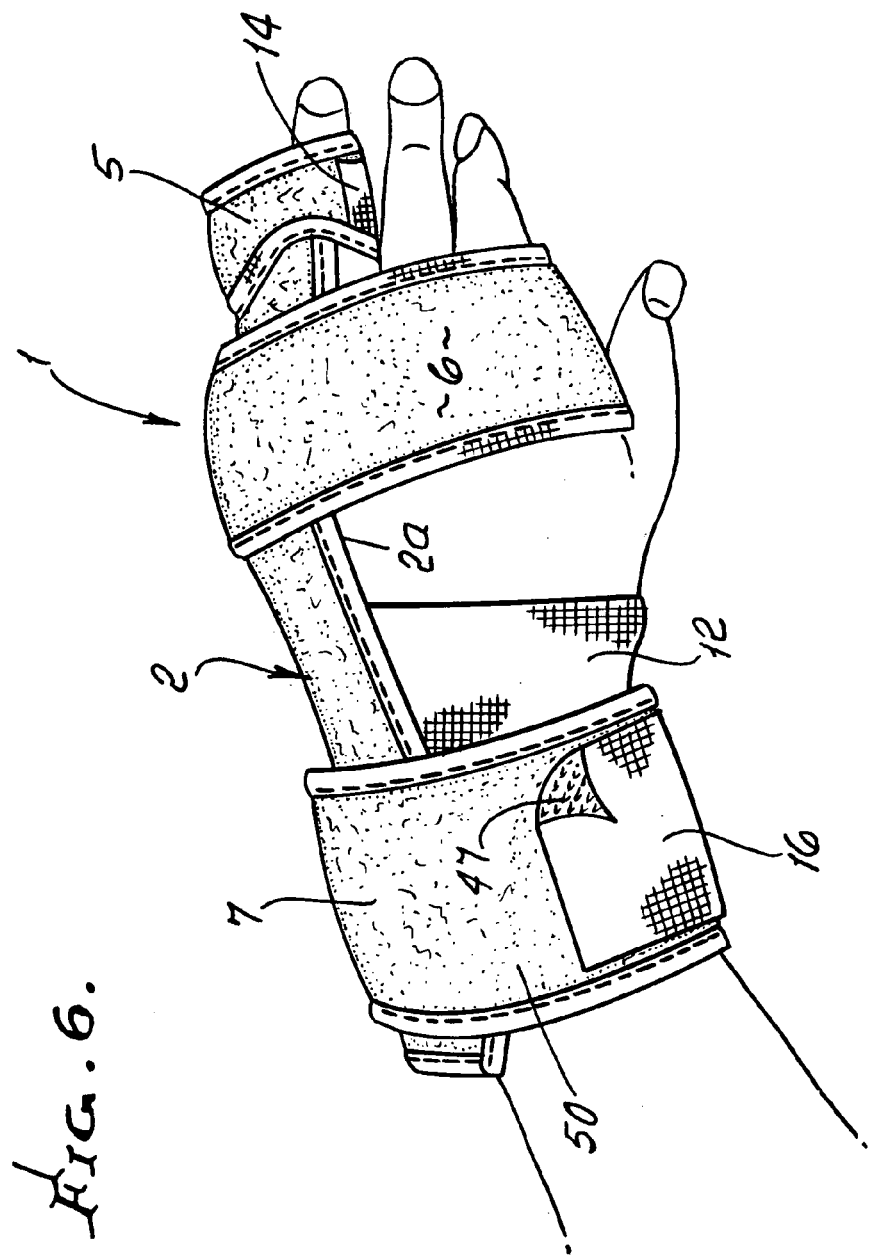
FIG. 6 is a view like FIG. 5, but showing all straps wrapped in securing position.

FIG. 4 shows brace 1 further secured to the patient by wrapping strap 5 around the pinky and ring fingers of the patient's hand, and securing it to the elongated member 2, by locking mechanism 14. FIG. 5 shows brace 1 further secured to the patient by wrapping strap 6 across the palm and around the webbing between the thumb and hand, and it is then secured to the elongated member 2 by securing locking mechanism 15 to material at 49. As shown in FIG. 6, the brace 1 is further completely secured or anchored to the patient by wrapping strap 7 around the lower arm or wrist of the patient and securing it to the elongated member 2 by locking mechanism 16 applied to 50. Strap 7 and the stiffeners brace the hand and anchor the wrist in fixed positions. The three straps are quickly and easily removable, for hand adjustment.

In an example, the elongated member 2 may be approximately eight and one/half inches long, and six inches wide across the hand, and three inches wide across the fingers. The two semi-rigid inserts may consist of moldable aluminum, to be encased along the volar and dorsal aspects of the brace (one on each side), measuring about eight inches in length, and one inch in width.

The first strap 5, may be about three-fourths inches wide, and eight inches long, and attached to the dorsum of the proximal end for circumferential support of the fourth and fifth fingers, the ring and pinky fingers. The second strap 6 may be about one and one eighth inch wide and thirteen and one-half inches long and is attached to the dorsal middle one third of the brace. It wraps around the palm, reattaching to the dorsal side of the brace 1. The third strap 7 is attached at the dorsal side of the proximal end and provides circumferential support to the wrist area, and is preferably about one and one-half inch wide and thirteen and one-half inches long.

In summary the finger and hand brace include:
a) a longitudinally elongated brace body, adapted to be applied lengthwise to the wrist and finger region of the hand,
b) multiple flexible flaps carried by the body to be spaced lengthwise thereof and to extend from the body,
c) separate flaps configured to be securely wrapped about at least two of the following:
  i) hand
  ii) wrist
  iii) a finger or fingers,
d) and retention means on the brace to retain the flaps in wrapped condition.

Three of such flaps are preferred, to wrap as referred to.

One or more longitudinally elongated stiffeners may be carried by said body; and a pocket or pockets are provided in the body to receive the stiffeners, two of the straps wrapping about two pockets and stiffeners therein. Such stiffeners are substantially inflexible.

Also provided is or are retention means located at flap terminals. Such retention means may comprise tabs projecting from flap terminals; and such tabs may include or carry hook or pile material. Sleeves are provided on the body to receive and position the user's wrist and at least one finger, to be wrapped by flaps.

Figure 9:
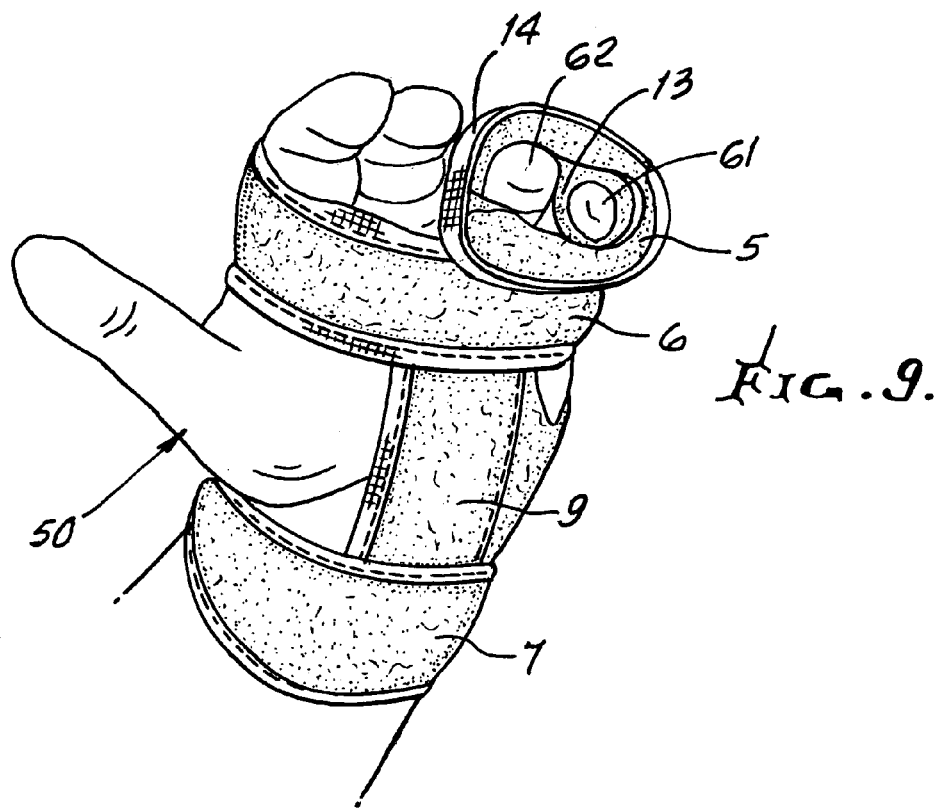
Figure 10:
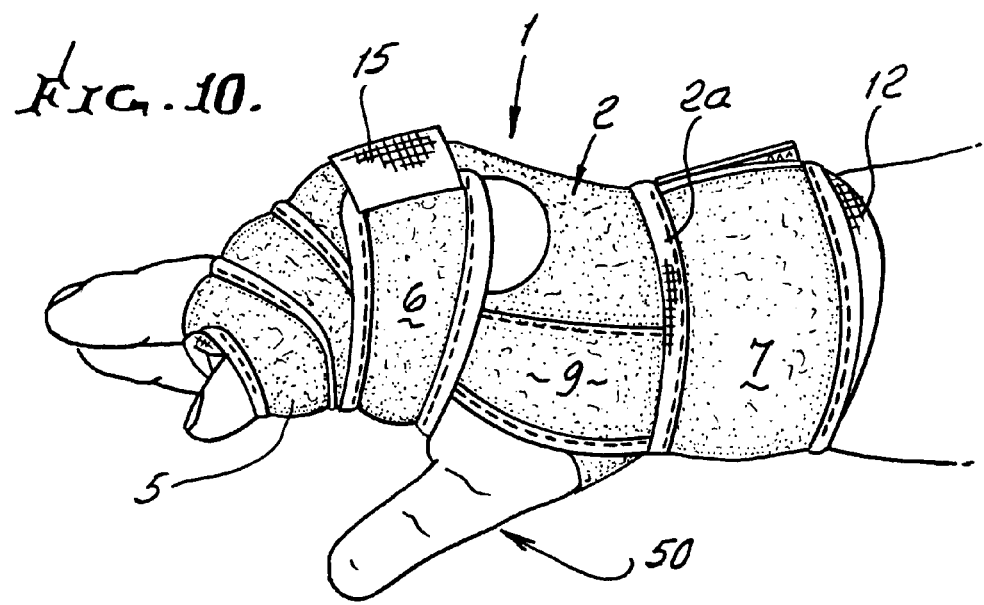
Figure 17:
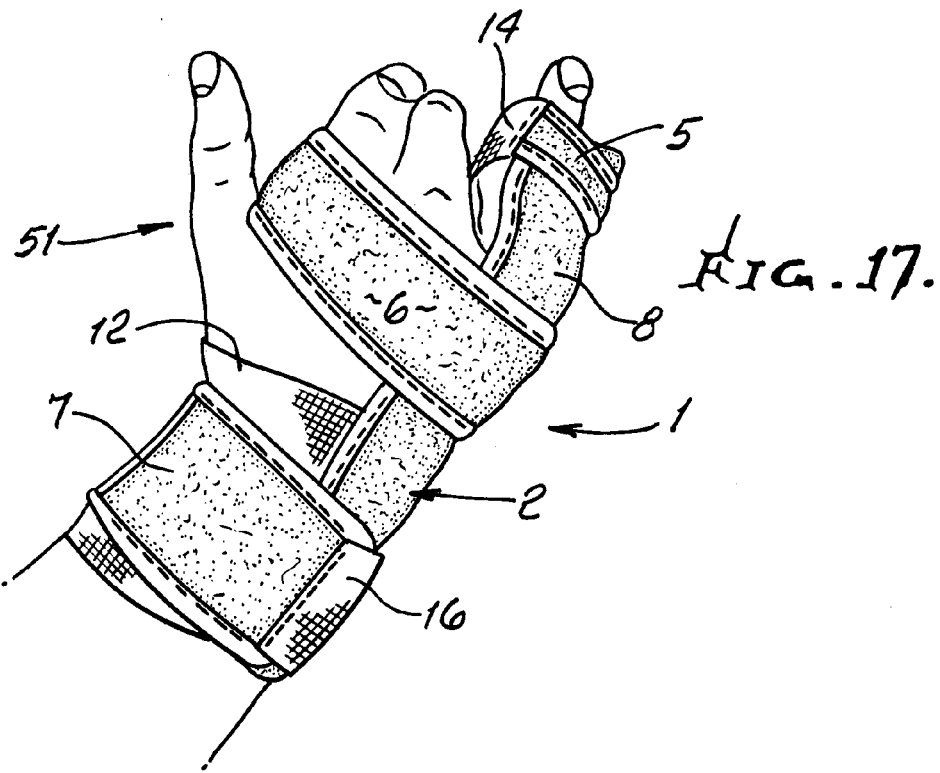

It will be understood that the brace 1 of the invention is applicable to either the left hand, or right hand, in various fracture modes. For example, FIGS. 9 and 10 are views showing the brace of the invention applied to the left hand 50 that has undergone a boxer fracture. The view (metacarpal 4 and 5) is otherwise described as a "left lateral, outside". A boxer fracture may be described as a traumatic fracture of the fifth metacarpal bone, at the shaft and neck of that bone. Such a fracture usually results from punching activity. Note strap 6 wrapped about the palm of the hand; strap 5 wrapped about the first and second fingers 61 and 62; and strap 7 wrapped about the wrist. FIG. 17 is another similar view.

Figure 11:
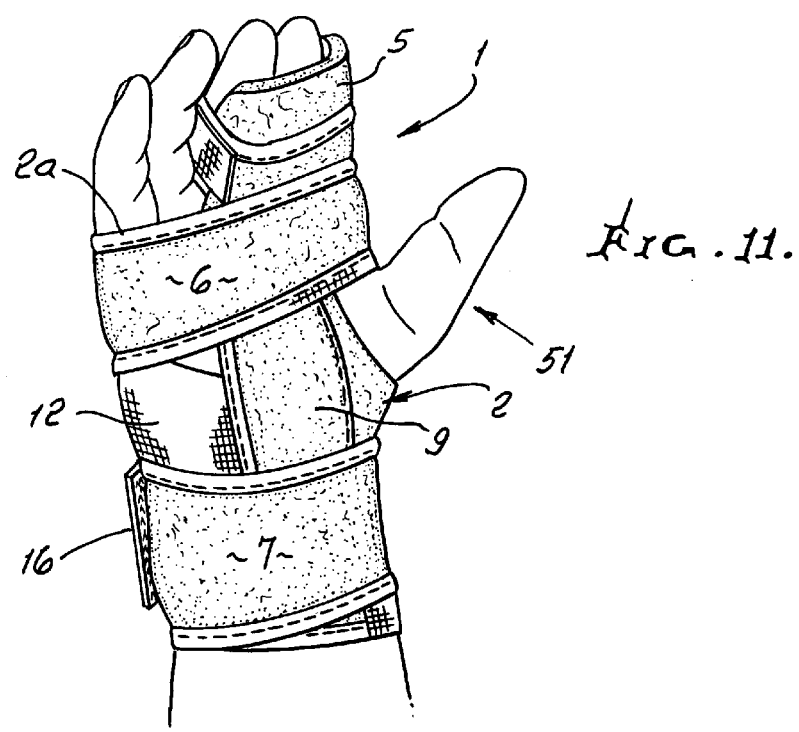
Figure 12:
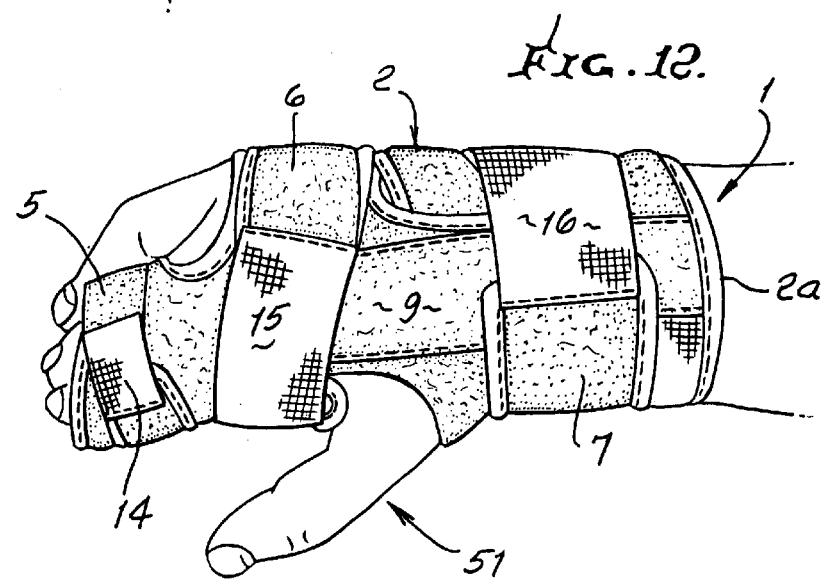
Figure 18:
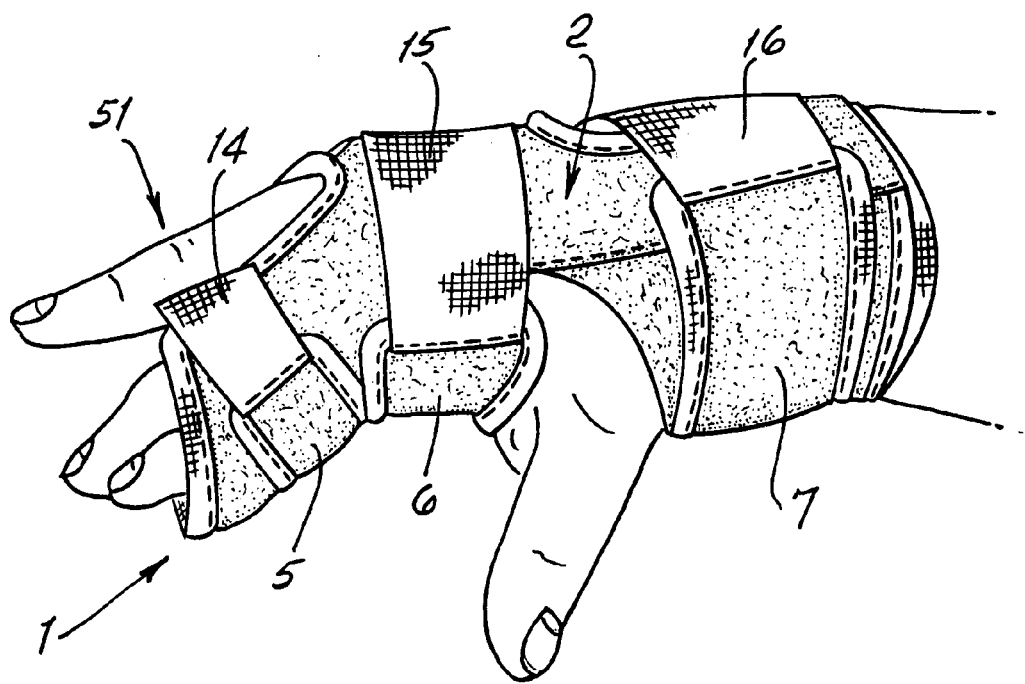

FIGS. 11 and 12 are views of the brace 1 applied to the right hand 51 that has undergone a metacarpal 2 and 3 fracture, the view otherwise referred to as a "right medial inside" view. Note the wrapped positions of the straps 5, 6, and 7, relative to the right hand 51. FIG. 18 is another similar view.

Figure 13:
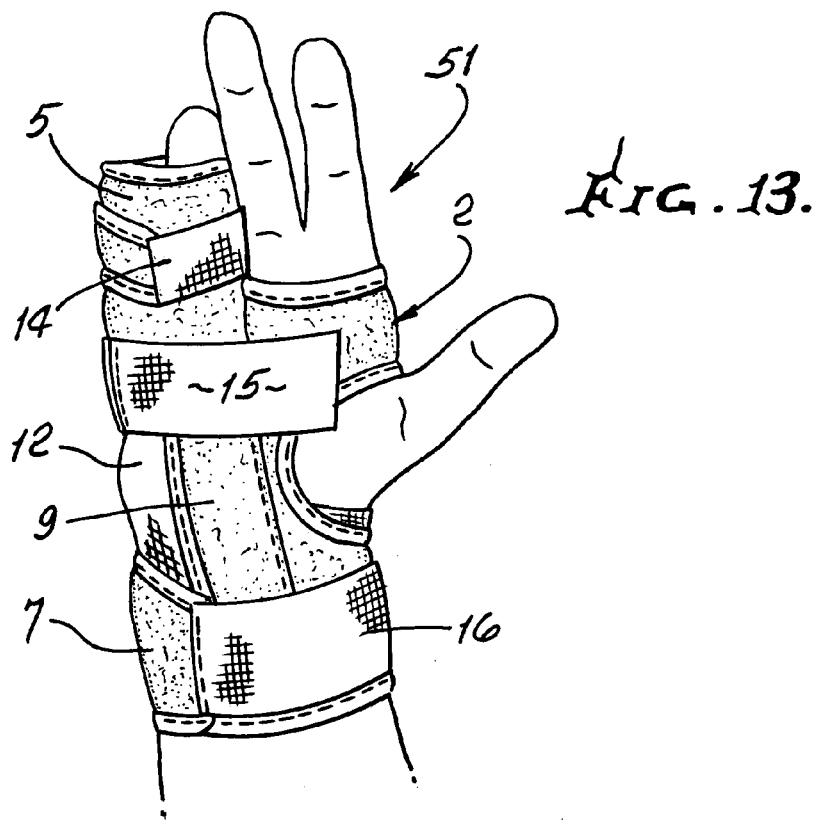
Figure 14:
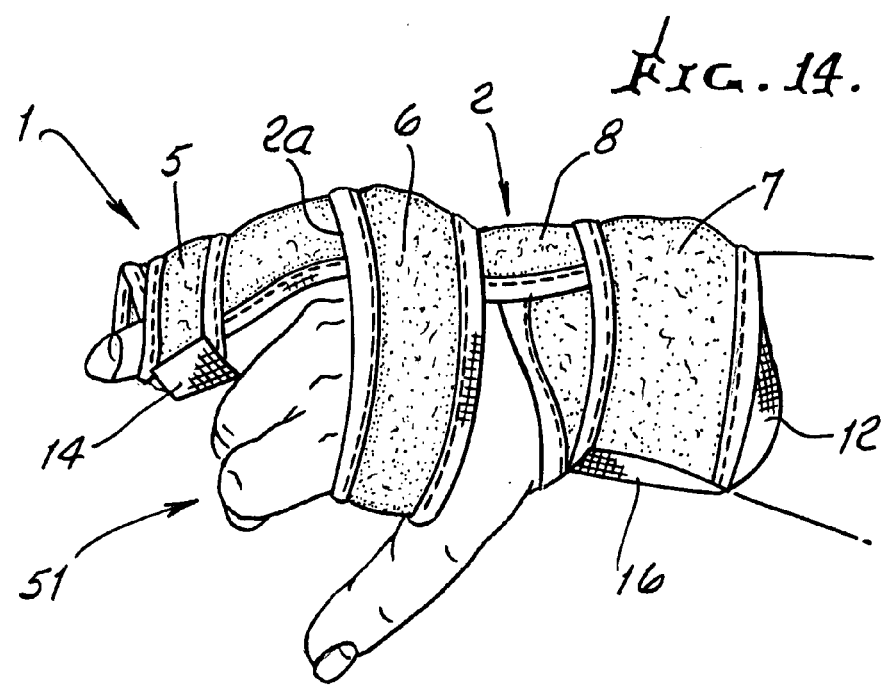

FIGS. 13 and 14 are views of the brace 1 applied to the right hand 51 that has undergone a boxer (metacarpal 4 and 5) fracture, that view otherwise referred to a "right lateral outside" view. Note the wrapped positions of the straps 5, 6 and 7 relative to the right hand.

FIGS. 15 and 16 are views of the brace 1, applied to the left hand 50 that has undergone a metacarpal 2 and 3 fracture, that view otherwise referred to as "left medial inside" view. Note the hand immobilizing positions of the three wrapped straps 5, 6 and 7 relative to the left hand structure as shown.

Although the present invention has been described in considerable detail with reference to certain preferred versions thereof, other versions are possible. Therefore, the spirit and scope of the invention should not be limited to the description of the preferred versions contained herein.

The invention further provides a multiple use reversible gauntlet brace, that can be used to immobilize metacarpal 4 and/or 5 and proximal phalange or phalanges 4 and/or 5 on the right hand, and metacarpal 2 and/or 3 and proximal phalange or phalanges 2 and 3 on the left hand. When turned over, the reversible brace can be used to immobilize metacarpal 4 and/or 5 and proximal phalange or phalanges 4 and 5 on the left hand, and metacarpal 2 and/or 3 and proximal phalange or phalanges 2 and/or 3 on the right hand. Malleable stays in or on the brace are typically bent or re-bent to conform to the selected use, prior to application of the brace to the hand and wrist.

When using the brace for $4^{th}$ and $5^{th}$ metacarpal fractures, the through opening 60 in body 2, between the stays, in lateral alignment with 6, as seen in FIG. 1, is not used. However, when the brace is used for the $2^{nd}$ and $3^{rd}$ metacarpal fractures, the thumb opening receives the user's thumb. See FIGS. 11, 12 and 18 for right hand, and see FIGS. 15 and 16 for left hand.

We claim:
1. In a finger and hand brace, the combination comprising:
a) a longitudinally elongated brace body, adapted to be applied lengthwise to the wrist and finger regions of the hand, b) multiple flexible flaps carried by the body to be spaced lengthwise thereof and to extend from the body, c) the multiple flexible flaps are separate flaps and are configured to be securely wrapped about at least two of the following: i) hand ii) wrist iii) a finger or fingers, d) and retention means on the brace to retain the flaps in wrapped condition, e) two elongated stiffeners and elongated pockets receiving the stiffeners and carried by the body, f) a first sleeve carried by the body in wrapping alignment with one strap to receive the user's hand, and an auxiliary sleeve carried by the body in wrapping alignment with another strap to receive a user's finger, g) said auxiliary sleeve located substantially between said two stiffeners h) said first sleeve substantially bridging said two stiffeners.

2. The combination of claim 1 wherein said elongated stiffeners are carried by said body to extend crosswise of wrapped flaps.

3. The combination of claim 2 wherein two of the straps are positioned to be wrapped about the pockets, stiffeners therein, and body material associated therewith.

4. The combination of claim 3 wherein the stiffeners are malleable.

5. The combination of claim 1 wherein said retention means are located at the end of the flaps.

6. The combination of claim 5 wherein said retention means comprise tabs projecting from the ends.

7. The combination of claim 6 wherein said tabs support hook or pile material.

8. The combination of claim 1 wherein there are three of said flaps, to respectively wrap about the hand, wrist, and a certain finger or fingers.

9. The combination of claim 1 wherein said auxiliary sleeve is carried by the body to position said finger to be wrapped by one of the flaps, said sleeves spaced apart longitudinally.

10. The combination of claim 1 wherein said body and flaps are configured to allow selective application to both the user's left and right hands.

* * * * *